(12) United States Patent
Shimada et al.

(10) Patent No.: US 11,167,108 B2
(45) Date of Patent: Nov. 9, 2021

(54) MEDICINE INJECTION CATHETER AND MEDICINE INJECTION SYSTEM

(71) Applicant: TERUMO KABUSHIKI KAISHA, Tokyo (JP)

(72) Inventors: Naoya Shimada, Kanagawa (JP); Naoki Ishii, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 213 days.

(21) Appl. No.: 16/126,531

(22) Filed: Sep. 10, 2018

(65) Prior Publication Data

US 2019/0009056 A1 Jan. 10, 2019

Related U.S. Application Data

(63) Continuation of application No. PCT/JP2017/009686, filed on Mar. 10, 2017.

(30) Foreign Application Priority Data

Mar. 11, 2016 (JP) .............................. JP2016-047971

(51) Int. Cl.
*A61M 25/00* (2006.01)
*A61M 39/26* (2006.01)
(Continued)

(52) U.S. Cl.
CPC ...... *A61M 25/0084* (2013.01); *A61M 5/3202* (2013.01); *A61M 5/329* (2013.01);
(Continued)

(58) Field of Classification Search
CPC .. A61M 2025/0073; A61M 2205/3344; A61M 25/0084; A61M 25/0108;
(Continued)

(56) References Cited

U.S. PATENT DOCUMENTS 5,336,222 A 8/1994 Durgin, Jr. et al.
5,725,524 A 3/1998 Mulier et al.
(Continued)

FOREIGN PATENT DOCUMENTS

JP 2004528062 A 9/2004
JP 2009291373 A 12/2009
(Continued)

OTHER PUBLICATIONS

An English Translation of the International Search Report (Form PCT/ISA/210) and the Written Opinion of the International Searching Authority (Form PCT/ISA/237) dated Jun. 13, 2017 by the Japanese Patent Office in corresponding International Application No. PCT/JP2017/009686 (5 pages).
(Continued)

*Primary Examiner* — Lauren P Farrar
*Assistant Examiner* — Hamza A Darb
(74) *Attorney, Agent, or Firm* — Buchanan Ingersoll & Rooney PC (57) ABSTRACT

A medicine injection catheter includes: a catheter main body formed with a medicine supply lumen; a tubular body connected to the distal end of the catheter main body and having a lumen communicating with the medicine supply lumen; an injection needle connected to the tubular body; a tubular cover member that accommodates the tubular body and that is configured to be advanced and retracted in the axial direction of the catheter main body between a first position where a distal end of the injection needle is accommodated in the tubular cover and a second position where the distal end of the injection needle protrudes forward from the inside space; a closing member to close and open the lumen of the tubular body, a motion conversion mechanism which converts advancing/retracting motion of the cover
(Continued)

member into movement of the closing member to close the lumen of the tubular body.

17 Claims, 5 Drawing Sheets

(51) Int. Cl.
*A61M 5/32* (2006.01)
*A61M 5/34* (2006.01)
*A61M 25/04* (2006.01)
*A61M 25/01* (2006.01)

(52) U.S. Cl.
CPC ........ *A61M 5/345* (2013.01); *A61M 25/0108* (2013.01); *A61M 25/04* (2013.01); *A61M 39/26* (2013.01); *A61M 2025/0089* (2013.01); *A61M 2039/267* (2013.01); *A61M 2205/3344* (2013.01); *A61M 2210/125* (2013.01)

(58) Field of Classification Search
CPC ............ A61M 39/26; A61M 2039/267; A61M 5/329; A61M 5/345; A61M 5/3202; A61M 2025/0089; A61M 2210/125; A61M 2005/3103
See application file for complete search history.

(56) References Cited

U.S. PATENT DOCUMENTS

| | | | |
|---|---|---|---|
| 2003/0195469 A1* | 10/2003 | Altman | A61M 25/0144 604/164.02 |
| 2005/0263188 A1* | 12/2005 | Sesser | G05D 16/0688 137/505.25 |
| 2009/0259212 A1 | 10/2009 | Sabbah | |
| 2009/0306473 A1 | 12/2009 | Tanaka et al. | |
| 2015/0258270 A1* | 9/2015 | Kunis | A61M 25/0074 604/506 |

FOREIGN PATENT DOCUMENTS

| | | |
|---|---|---|
| JP | 2011516205 A | 5/2011 |
| WO | 2004020032 A1 | 3/2004 |

OTHER PUBLICATIONS

The extended European Search Report dated Sep. 16, 2019, by the European Patent Office in corresponding European Patent Application No. 17763423.5-1122. (7 pages).
International Search Report (PCT/ISA/210) dated Jun. 13, 2017, by the Japanese Patent Office as the International Searching Authority for International Application No. PCT/JP2017/009686.
Written Opinion (PCT/ISA/237) dated Jun. 13, 2017, by the Japanese Patent Office as the International Searching Authority for International Application No. PCT/JP2017/009686.

* cited by examiner

MEDICINE INJECTION CATHETER AND MEDICINE INJECTION SYSTEM

CROSS-REFERENCES TO RELATED APPLICATIONS

This application is a continuation of International Application No. PCT/JP2017/009686 filed on Mar. 10, 2017, which claims priority to Japanese Application No. 2016-047971 filed on Mar. 11, 2016, the entire content of both of which is incorporated herein by reference.

TECHNICAL FIELD

This invention generally relates to a medicine or drug injection catheter, particularly to a medicine injection catheter for injecting medicine or a medication through a body wall of a living body. In addition, this invention also generally involves a medicine injection using such a medicine injection catheter.

BACKGROUND DISCUSSION

As a therapeutic method for so-called cardiac insufficiency in which the pumping function of the heart is damaged by various causes and the heart is unable to feed out a quantity of blood necessary for tissue metabolism on a whole body basis, a method of injecting a drug including a biomaterial such as a growth factor, a gene or cells to the injured part such as an infarcted area of the heart has been investigated and paid attention to.

While such a drug can be injected to the heart by thoracotomy, Japanese Patent Application Publication No. 2004-528062 discloses a medical instrument provided with a puncture apparatus at the distal end of a catheter for reducing invasiveness. A needle-shaped device of the puncture apparatus is made to puncture a body wall such as cardiac muscle, and the drug is injected through the puncture device.

SUMMARY

However, there is a problem that the procedure of making the needle-shaped device puncture the body wall is complicated, and the procedure time is prolonged.

In addition, since it is impossible to confirm whether or not the needle-shaped device has punctured the body wall, there is a possibility of leakage of the drug to the surroundings of the body wall before or after the puncture by the needle-shaped device. If the drug leaks to the surroundings of the body wall, a new disease may be generated, or it may become difficult to administer an appropriate quantity of the drug to a target site.

The medicine injection catheter disclosed here allows medicine to be reliably injected through a body wall of a living body with a simple procedure and without leakage of the medicine.

The disclosure here also provides a medicine injection system using such a medicine injection catheter.

A medicine injection catheter according to one aspect of the disclosure includes medicine injection catheter for injecting medicine through a wall of a living body. The medicine injection catheter comprises: an elongated catheter main body extending in an axial direction, wherein the catheter main body includes a medicine supply lumen; a tubular body connected to the distal end of the catheter main body, wherein the tubular body includes a lumen communicating with the medicine supply lumen; an injection needle connected to the distal end of the tubular body; a tubular cover member that includes an inside space in which is accommodated at least the tubular body, with the tubular cover member being disposed at a distal end portion of the catheter main body and being configured to undergo advancing/retracting motion along the axial direction of the catheter main body to move between a first position in which the distal end of the injection needle is accommodated in the inside space and a second position in which the distal end of the injection needle protrudes distally beyond the distal end of the catheter main body and outside the inside space; and a closing member configured to close and open the lumen of the tubular body by moving within the inside space of the cover member in a radial direction intersecting the axial direction of the catheter main body. A motion conversion mechanism converts the advancing/retracting motion of the cover member relative to the catheter main body into a moving motion of the closing member so that the closing member closes the lumen of the tubular body when the cover member is located at the first position and opens the lumen of the tubular when the cover member is located at the second position. An elastic member is disposed between the catheter main body and the cover member and elastically presses the cover member relative to the catheter main body toward the first position.

A configuration may be adopted such that: the tubular body is flexible; the closing member includes at least one leaf spring which is attached to an inner surface of the cover member and which presses the tubular body from an outer circumferential portion to close the lumen of the tubular body; the motion conversion mechanism includes an inclined surface formed in the catheter main body such as to be inclined relative to the axial direction of the catheter main body; and when the cover member is located at the first position, the at least one leaf spring is separated from the inclined surface to close the lumen of the tubular body, whereas when the cover member is located at the second position, the at least one leaf spring is guided by the inclined surface and elastically deformed to such an extent as to be separated from the outer circumferential portion of the tubular body, thereby opening the lumen of the tubular body.

Alternatively, a configuration may be adopted such that: the tubular body is flexible; the closing member includes at least one leaf spring which is attached to the catheter main body and which presses the tubular body from an outer circumferential portion to close the lumen of the tubular body; the motion conversion mechanism includes a projecting member which is attached to an inner surface of the cover member and which extends in the axial direction of the catheter main body toward the at least one leaf spring; and when the cover member is located at the first position, the at least one leaf spring is separated from the projecting member to close the lumen of the tubular body, whereas when the cover member is located at the second position, the at least one leaf spring is pressed by the projecting member and elastically deformed to such an extent as to be separated from the outer circumferential portion of the tubular body, thereby opening the lumen of the tubular body.

The closing member preferably includes a pair of leaf springs which pinch an outer circumferential portion of the tubular body from both sides, or the closing member preferably includes one leaf spring that presses an outer circumferential portion of the tubular body from one side.

Preferably, the cover member has a partition plate which is fixed in the inside space vertically to the axial direction of the catheter main body and which is formed with a through-hole permitting the injection needle to pass therethrough, and the elastic member is disposed between a front end portion of the catheter main body and the partition plate of the cover member.

The medicine injection catheter may further include a trap mechanism that establishes a negative pressure in the inside space of the cover member to trap a body wall surface of the living body at a front end portion of the cover member.

Besides, the catheter main body and the cover member each preferably have a contrast marker, such that movements of the cover member and puncture of a body wall such as cardiac muscle by the needle can be confirmed externally, and information about the torsion and orientation of the catheter main body, particularly its distal end portion, can be given to the operator according to the manner in which a pattern of the contrast markers or the like is seen.

A medicine injection system according to the invention includes: the above-mentioned medicine injection catheter; a pressure gauge for detecting a pressure in the medicine supply lumen of the medicine injection catheter; a medicine supply section that supplies medicine into the medicine supply lumen of the medicine injection catheter; and a control section that controls supply of the medicine by the medicine supply section in such a manner that the pressure in the medicine supply lumen of the medicine injection catheter, the pressure being detected by the pressure gauge, is to be constant.

According to the medicine injection catheter disclosed here, the cover member having the inside space is disposed to be capable of being advanced and retracted between the first position where the distal end of the injection needle is accommodated in the inside space and the second position where the distal end of the injection needle protrudes forward from the inside space. In addition, the motion conversion mechanism converts an advancing/retracting motion of the cover member relative to the catheter main body into a moving motion of the closing member, such as to close the lumen of the tubular body by the closing member when the cover member is located at the first position and to open the lumen of the tubular body when the cover member is located at the second position. Therefore, medicine can be reliably injected through a body wall of a living body with an easy procedure and without leakage of the medicine.

According to another aspect, a medicine injection catheter for injecting medicine through a wall of a living body comprises: a catheter main body extending in an axial direction, with the catheter main body including a medicine supply lumen configured to receive medicine supplied from a medicine supply, and the medicine supply lumen extending in the catheter main body and opening at the distal end of the catheter main body; a tubular body connected to the catheter main body and including a lumen in communication with the medicine supply lumen so that medicine in the medicine supply lumen of the catheter main body flows into the lumen in the tubular body, with the tubular body being comprised of a material that is deformable upon application of a force to the outer periphery of the tubular body to close the lumen in the tubular body and prevent the medicine from flowing through the lumen in the tubular body; and an injection needle connected to the tubular body. The catheter main body, the tubular body and the injection needle are movable together as a unit. A tubular cover surrounds an interior in which is located at least a portion of the tubular body, with the tubular cover and the catheter main body being relatively movable between a first position in which a distal-most end of the injection needle is proximal of a distal-most end of the tubular cover so that the distal-most end of the injection needle is covered by the tubular cover and a second position in which the distal-most end of the injection needle protrudes distally beyond the distal-most end of the catheter main body so that the distal-most end of the injection needle is outside the tubular cover to puncture the living body. A spring applies a biasing force between the tubular cover and the catheter main body to urge the catheter main body towards the first position relative to the catheter main body, and at least one projection is fixed to the catheter main body or the tubular cover and extends inwardly toward the central axis of the tubular body. The at least one projection contacts the outer periphery of the tubular body when the catheter main body is in the first position relative to the catheter main body so that the at least one projection applies a force to the tubular body that deforms the tubular body and closes the lumen in the tubular body to prevent the prevent the medicine from flowing through the lumen in the tubular body, and the at least one projection is spaced apart from the outer periphery of the tubular body when the catheter main body is in the second position relative to the catheter main body so that the lumen in the tubular body is open to permit the medicine to flow through the lumen in the tubular body toward the injection needle.

In accordance with another aspect, a method comprises: inserting a catheter main body into a patient's body, wherein the catheter main body includes a medicine supply lumen extending in the catheter main body and opening at the distal end of the catheter main body, the catheter main body being connected to a tubular body which includes a lumen in communication with the medicine supply lumen, the tubular body being connected to an injection needle which possesses a distal end, the catheter main body and the injection needle being movable together, at least a portion of the tubular body being positioned in an interior of a tubular cover. The method further comprises moving the tubular cover and the catheter main body in a forward direction toward a wall inside the patient's body while a force is applied to the tubular body to close the lumen in the tubular body to completely block flow of medicine through the lumen in the tubular body; moving the tubular cover in the forward direction so that a distal end of the tubular cover contacts the wall inside the patient's body to stop the movement of the tubular cover in the forward direction, and moving the catheter main body in the forward direction relative to the tubular cover after the distal end of the tubular cover contacts the wall inside the patient's body so that the distal end of the injection needle extends distally beyond a distal end of the tubular cover and punctures the wall of the patient's body. The moving of the catheter main body in the forward direction relative to the tubular cover automatically removing the force applied to the tubular body to open the lumen in the tubular body. The method also comprises, following the opening of the lumen in the tubular body, the medicine flowing through the medicine supply lumen, through the lumen in the tubular body and through the injection needle so that the medicine exits the injection needle by way of the distal end of the injection needle and is introduced into tissue in the wall of the patient's body.

DETAILED DESCRIPTION

Set forth below with reference to the accompanying drawings is a detailed description of embodiments of a medicine injection catheter and medicine injection system, representing examples of the inventive medicine injection catheter and medicine injection system disclosed here.

Embodiment 1

Figure 1:
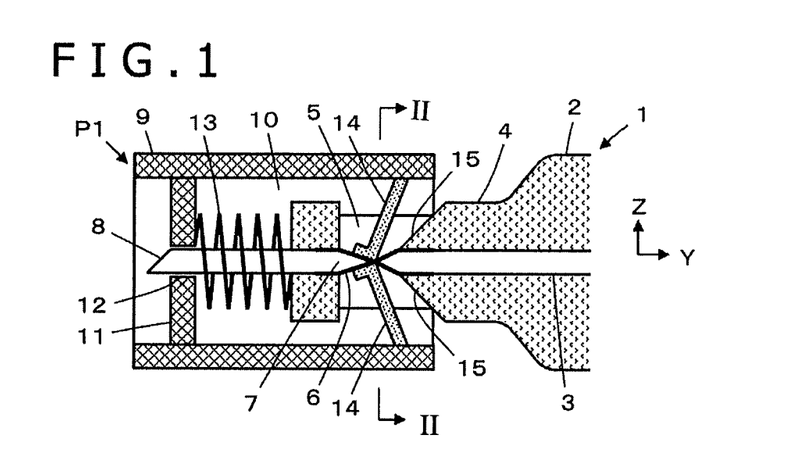
FIG. 1 is a cross-sectional view of a medicine injection catheter according to Embodiment 1 when a cover member is located at a first position.

FIG. 1 depicts the configuration of a medicine injection catheter 1 according to Embodiment 1. The medicine injection catheter 1 includes an elongated catheter main body 2, and a medicine supply lumen 3 extending along an axial direction of the catheter main body 2 is formed inside the catheter main body 2.

The catheter main body 2 has at its distal end a reduced diameter portion 4 possessing an outer diameter smaller than the outer diameter of another portion of the reduced diameter portion 4 that is proximal the reduced diameter portion 4. The reduced diameter portion 4 is formed with an opening portion (through opening) 5 which penetrates the reduced diameter portion 4 in a direction orthogonal to the axial direction of the catheter main body 2. By virtue of the opening portion 5, the medicine supply lumen 3 is divided, and a tubular body 6 is disposed at the divided portion of the medicine supply lumen 3.

The tubular body 6 is formed of a flexible soft tube, and, at both end portions of the tubular body 6, a lumen 7 of the tubular body 6 communicates with the medicine supply lumen 3, whereby the divided medicine supply lumen 3 is connected. In addition, an injection needle 8 is held by a distal end portion of the catheter main body 2, and is connected to the tubular body 6 either directly or through the medicine supply lumen 3. Thus, the lumen in the injection needle 8, the lumen in the tubular body 6 and the lumen 3 in the catheter main body 2 are in communication with one another.

Here, for convenience, the axial direction of the catheter main body 2 is referred to as the Y-direction, the direction in which the opening portion 5 penetrates the reduced-diameter portion 4 is referred to as the Z-direction, and the direction orthogonal to the YZ plane is referred to as the X-direction.

At a distal end portion of the catheter main body 2, a cylindrical cover member (tubular cover) 9 having a center axis that is coaxial with the catheter body 2 is disposed in such a manner as to surround the reduced-diameter portion 4. The cover member 9 has an inside space or interior 10 that accommodates the reduced-diameter portion 4, and the cover member 9 may include, in the inside of the cover member 9 in the vicinity of a distal end portion of the cover member 9, with a partition plate 11 extending along the XZ direction in such a manner as to bisect the inside space 10 in the Y-direction. In the center of the partition plate 11, a through-hole 12 in the Y-axis direction which has a diameter (inner diameter) larger than the outside diameter of the injection needle 8 may be provided, and the injection needle 8 passes through the through-hole 12.

In addition, an elastic member 13 composed of a coil-shaped spring (coil spring) is disposed between the partition plate 11 of the cover member 9 and a front end portion of the catheter main body 2, and the injection needle 8 penetrates or passes through the inside of the elastic member 13. The elastic member 13 is not limited to being a spring, and need only be a member that has elasticity.

Further, a pair of leaf springs or projections 14 constituting a closing member for closing and opening the lumen 7 of the tubular body 6 are disposed in the inside of the cover member 9 in the vicinity of a rear end portion of the cover member 9. These leaf springs 14 are disposed in the same position in the Y-direction. One of the leaf springs 14 is attached to that part of the inner surface of the cover member 9, which part is located on the most +Z-direction side (i.e., most positive Z direction side), and extends substantially in the −Z-direction (negative Z direction or downward direction in FIGS. 1 and 4 for example). The other leaf spring 14 is attached to that part of the inner surface of the cover member 9, which is located on the most −Z-direction side (most negative Z direction side), and extends substantially in the +Z-direction (i.e., the positive Z direction or the upward Z direction in FIGS. 1 and 4 for example). The two leaf springs 14 may thus be attached to the inner surface of the cover member 9 at diametrically opposite locations. Each of the leaf springs 14 can be elastically deformed in the Y-direction and the Z-direction.

In addition, the catheter main body 2 is formed with a pair of inclined surfaces (contact parts) 15 which are inclined relative to the axial direction of the catheter main body 2 and front on the opening portion 5. The pair of inclined surfaces 15 constitute a motion conversion mechanism for converting an advancing/retracting motion of the cover member 9 relative to the catheter main body 2 into moving motions of the pair of leaf spring 14. One of the inclined surfaces 15 is located on the +Z-direction side relative to the medicine supply lumen 3, and is directed in the −Y-direction (i.e., the negative Y direction or the leftward Y direction in FIGS. 1 and 4 for example) and +Z-direction. The other inclined surface 15 is located on the −Z-direction side relative to the medicine supply lumen 3, and is directed in the −Y-direction and the −Z-direction.

Figure 2:
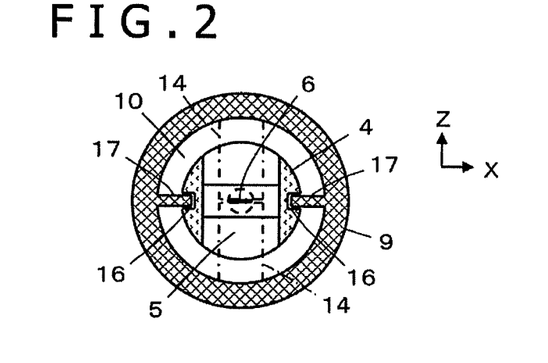
FIG. 2 is a cross-sectional view taken along the section line II-II of FIG. 1.

As depicted in FIG. 2, an outer circumferential surface of the reduced-diameter portion 4 of the catheter main body 2 includes a pair of cover member guide grooves 16 extending in the Y-direction at a +X-directional end portion and a −X-directional end portion of the reduced-diameter portion 4. The inner surface of the cover member 9 is formed, at a +X-directional end portion and a −X-directional end portion thereof, with a pair of projections (guide projections) 17 which project in the X-direction toward the inside space 10 of the cover member 9 and extend in the Y-direction.

Figure 3:
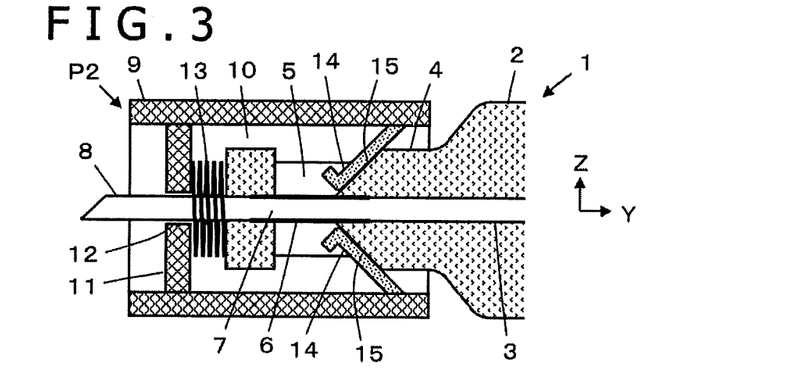
FIG. 3 is a cross-sectional view depicting the medicine injection catheter according to Embodiment 1 when the cover member is located at a second position.

In addition, with the pair of projections 17 of the cover member 9 positioned respectively in the pair of cover member guide grooves 16, the cover member 9 is held by the catheter main body 2 in such a manner as to be capable of being advanced and retracted along the axial direction of the catheter main body 2, between a first position P1 where a −Y-direction side distal end of the injection needle 8 is accommodated in the inside space 10 as depicted in FIG. 1 and a second position P2 where the −Y-direction side distal end of the injection needle 8 projects forward, or in the −Y-direction, from the inside space 10 as depicted in FIG. 3.

When the cover member 9 is located at the first position P1 depicted in FIG. 1, the distal ends of the pair of leaf springs 14 of the cover member 9 pinch and press the tubular body 6 disposed in the opening portion 5 of the catheter main body 2 from both sides in regard of the Z-direction, whereby the tubular body 6 formed of a soft tube (a tube made of a material that deforms when the leaf springs 14 apply a force to the outer periphery of the tubular body 6) is crushed or inwardly deformed and the lumen 7 of the tubular body 6 is put into a closed state (occluded).

On the other hand, when the cover member 9 is located at the second position P2 depicted in FIG. 3, the pair of leaf springs 14 of the cover member 9 are guided respectively by the corresponding inclined surfaces 15 of the catheter main body 2, and are elastically deformed to such an extent that the distal ends of the leaf springs 14 are separated from the outer circumferential portion or outer periphery of the tubular body 6. By this, the lumen 7 of the tubular body 6 is put into an open state.

In other words, the lumen 7 of the tubular body 6 can be closed when the cover member 9 is located at the first position P1 and the −Y-direction side distal end of the injection needle 8 is accommodated in the inside space 10, and the lumen 7 of the tubular body 6 can be opened when the cover member 9 is located at the second position P2 and the −Y-direction side distal end of the injection needle 8 protrudes forward from the inside space 10.

In addition, by the coil-shaped elastic member 13 disposed between the partition plate 11 of the cover member 9 and the front end portion of the catheter main body 2, the cover member 9 is being elastically pressed forward in regard of the catheter main body 2, or in the −Y-direction, in relation to the catheter main body 2. When no external force is acting on the cover member 9, therefore, the cover member 9 is located at the first position P1 depicted in FIG. 1.

The material from which the catheter main body 2 is fabricated is preferably a material having a certain degree of flexibility, for example, a metal or a resin. Examples of the metal include pseudo-elastic alloys (inclusive of super-elastic alloys) such as Ni—Ti alloys, stainless steels (all kinds of SUS steels, such as SUS304, SUS303, SUS316, SUS316L, SUS316J1, SUS316J1L, SUS405, SUS430, SUS434, SUS444, SUS429, SUS430F, and SUS302), cobalt alloys, noble metals such as gold and platinum, tungsten alloys, and carbon materials (inclusive of piano wire).

Examples of the resin include polymer materials such as polyolefins (e.g., polyethylene, polypropylene, polybutene, ethylene-propylene copolymer, ethylene-vinyl acetate copolymer, ionomers, or mixtures of two or more of them), polyvinyl chloride, polyamides, polyamide elastomers, polyesters, polyester elastomers, polyurethane, polyurethane elastomers, polyimides, and fluororesins, or mixtures thereof, or at least two kinds of the polymer materials. Further examples of the resin include engineering plastics represented by polyether-ether ketone. In addition, the catheter main body 2 can include, for example, a multilayer tube including a composite material formed from these metals and/or resins.

The material from which the cover member 9 is fabricated may also be the same or similar materials to those used to fabricate the catheter main body 2.

The tubular body 6 may be formed from a material rich in flexibility, such as a silicone rubber.

The pair of leaf springs 14 are formed from a material having elasticity and rigidity sufficient for crushing flat (i.e., deforming) the tubular body 6 from the outer circumferential portion. Those metallic materials or resin materials which are general-purpose leaf spring forming materials can be used to fabricate the leaf springs 14.

Figure 4:
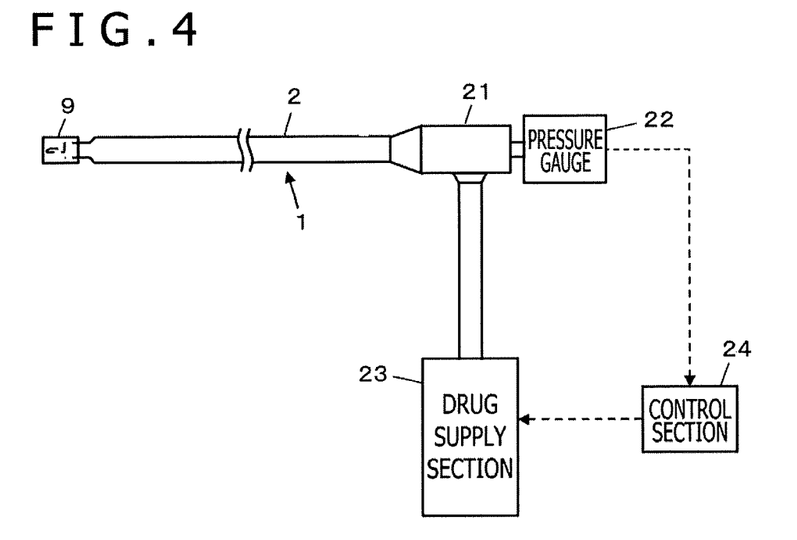
FIG. 4 is a block diagram depicting the configuration of a medicine injection system using the medicine injection catheter according to Embodiment 1.

Here, the configuration of a medicine injection system using the medicine injection catheter 1 according to Embodiment 1 is depicted in FIG. 4. A pressure gauge 22 and a medicine supply section 23 are connected to a proximal end portion of the medicine injection catheter 1 through a connector 21, and a control section 24 is connected to the pressure gauge 22 and the medicine supply section 23.

The pressure gauge 22 detects the pressure inside the medicine supply lumen 3 of the medicine injection catheter 1. The medicine supply section 23 includes, for example, a syringe pump, and supplies a medicine into the medicine supply lumen 3 of the medicine injection catheter 1. In addition, the control section 24 controls the supply of the medicine by the medicine supply section 23 in such a manner that the pressure inside the medicine supply lumen 3 of the medicine injection catheter 1 as detected by the pressure gauge 22 will be constant.

By the medicine injection system configured in this way, the pressure inside the medicine supply lumen 3 can be kept constant.

An example of an operation of the medicine injection catheter 1 according to Embodiment 1 will be described below.

Figure 5:
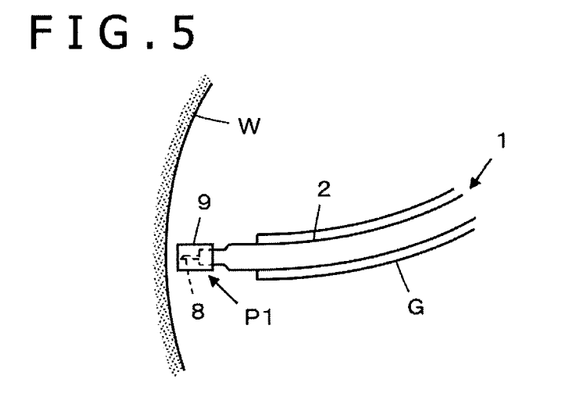
FIG. 5 is a figure depicting the medicine injection catheter according to Embodiment 1 in a state in which the cover member is set close to a body wall surface.

First, as depicted in FIG. 5, a guiding catheter G is inserted into the patient's body, for example, into the inside of the heart, the medicine injection catheter 1 is inserted into the guiding catheter G, and a distal end portion of the medicine injection catheter 1 is moved to a position at which the distal end portion of the medicine injection catheter 1 protrudes distally from the guiding catheter G.

It is assumed that the medicine supply lumen 3 of the medicine injection catheter 1 is filled with the medicine by the medicine supply section 23. It is to be noted that when the cover member 9 is not in contact with an inner wall W of the heart, no external force is acting on the cover member 9, so that the cover member 9 is located at the first position P1, the distal end of the injection needle 8 is accommodated in the inside space 10, and the lumen 7 of the tubular body 6 is in a closed state; therefore, leakage of the medicine from the injection needle 8 does not occur.

Figure 6:
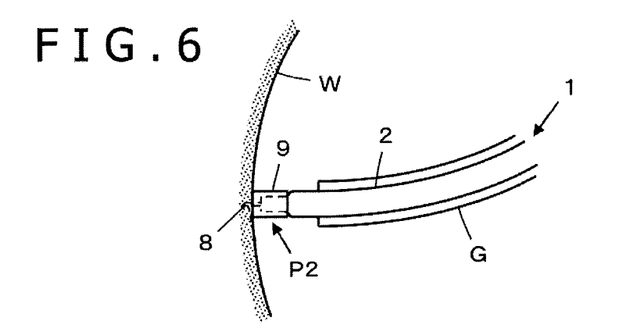
FIG. 6 is a figure depicting the medicine injection catheter according to Embodiment 1 in a state in which an injection needle punctures a body wall.

Then, when the medicine injection catheter 1 is moved forward to bring the distal end of the cover member 9 into contact with the inner wall W of the heart and, further, the medicine injection catheter 1 is pressed against the inner wall W of the heart as depicted in FIG. 6 to thereby move the cover member 9 to the second position P2, the distal end of the injection needle 8 protrudes forward from the inside space 10 to puncture the inner wall W of the heart, and the lumen 7 of the tubular body 6 is put into an open state (i.e., the lumen 7 is open). For this reason, the pressure inside the medicine supply lumen 3 is lowered, and, based on a detection signal from the pressure gauge 22 having detected the lowering in the pressure, the medicine supply section 23 is driven under control by the control section 24, whereby the supply of the medicine into the medicine supply lumen 3 is started. By this, the medicine in the medicine supply lumen 3 is injected into the heart tissue through the lumen 7 of the tubular body 6 and the injection needle 8.

When the inner wall W of the heart moves in the direction for separation from the medicine injection catheter 1, attendant on the beat of the heart, to be separated from the distal end of the cover member 9, the injection needle 8 is drawn out from the inner wall W of the heart and, simultaneously, the cover member 9 is moved from the second position P2 to the first position P1, so that the lumen 7 of the tubular body 6 is put into a closed state. Therefore, injection of the medicine from the injection needle 8 is stopped.

When the inner wall W of the heart moves again toward the medicine injection catheter 1, by the beat of the heart, to move the cover member 9 from the first position P1 to the second position P2, the distal end of the injection needle 8 protrudes forward from the inside space 10 to puncture the inner wall W of the heart and, simultaneously, the lumen 7 of the tubular body 6 is put into an open state, so that the medicine is injected into the heart tissue.

In this way, by the beating of the heart, injection of the medicine into the heart tissue and stopping of the injection are repeated.

When the cover member 9 is located at the first position P1 and the distal end of the injection needle 8 is accommodated in the inside space 10, the lumen 7 of the tubular body 6 is closed by the pair of leaf springs 14; on the other hand, when the cover member 9 is located at the second position P2 and the distal end of the injection needle 8 protrudes forward from the inside space 10, the lumen 7 of the tubular body 6 is opened. Therefore, without confirming whether or not the injection needle 8 is puncturing the inner wall W of the heart, the injection needle 8 is able to automatically puncture the inner wall W of the heart, synchronously with the beat of the heart, and the medicine can be reliably injected into the heat tissue. In addition, when the injection needle 8 is drawn out from the inner wall W of the heart, the injection of the medicine from the injection needle 8 automatically stops, and leakage of the medicine can be prevented. Accordingly, an appropriate amount of the medicine can be administered in a reliable manner, and unnecessary injection of the medicine into a part other than the target part can be prevented.

Further, since the injection of the medicine and the stopping of the medicine injection are automatically performed according to the movements of the cover member 9 relative to the catheter main body 2, simplification of the procedure can be achieved.

The tissue into which the medicine is injected is not limited to the heart. While it is possible in the case of the heart to inject the medicine substantially automatically through utilizing the heartbeat, the beat is not always required. In the case of other organs, also, it is possible to inject the medicine by pressing the catheter distal end against a body wall and to stop the injection by separating the catheter distal end from the body wall, so that simplification of the procedure and a safe procedure can be achieved.

Embodiment 2

In Embodiment 1 described above, the tubular body 6 is pinched and pressed from both sides by the pair of leaf springs 14 of the cover member 9 to thereby close the lumen 7 of the tubular body 6, but the invention is not limited in this regard. The lumen 7 of the tubular body 6 can be closed also by pressing an outer circumferential portion of the tubular body 6 from one side by one leaf spring 14.

Figure 7:
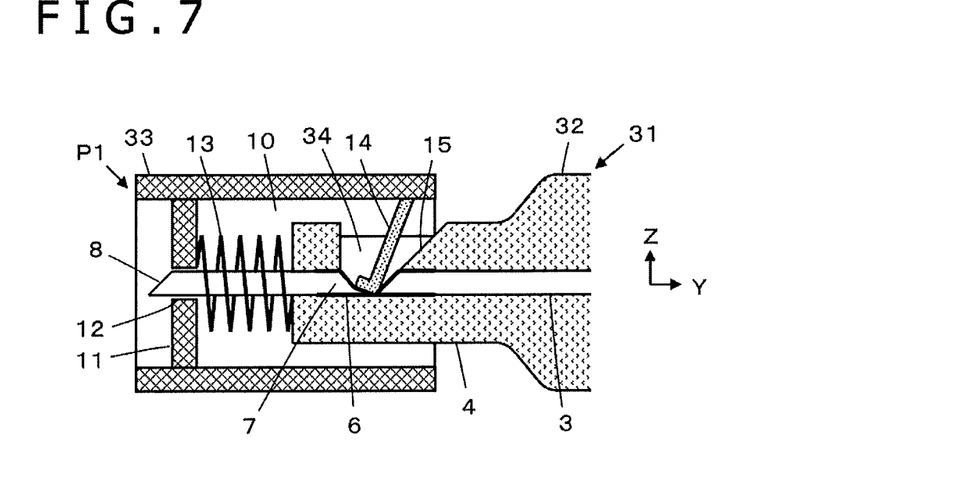
FIG. 7 is a cross-sectional view depicting a medicine injection catheter according to Embodiment 2 when a cover member is located at a first position.

FIG. 7 depicts the configuration of a medicine injection catheter 31 according to Embodiment 2. The medicine injection catheter 31 includes a cover member 33 disposed at a distal end portion of an elongated catheter main body 32 in such a manner as to be capable of being advanced and retracted.

Compared to the catheter main body 2 used in the medicine injection catheter 1 of Embodiment 1, the catheter main body 32 according to Embodiment 2 is configured in the same manner as the catheter main body 2 of Embodiment 1, except that the reduced-diameter portion 4 has a cutout 34 formed by cutting out only a part on the +1-direction side, instead of having the opening portion 5 fully penetrate in the Z-direction, and one inclined surface 15 fronting on the cutout 34 is formed. The tubular body 6 is disposed such as to be exposed in the cutout 34.

Compared to the cover member 9 used in the medicine injection catheter 1 of Embodiment 1, the cover member 33 of Embodiment 2 is configured in the same manner as the cover member 9 of Embodiment 1, except that one leaf spring 14 is provided on the +Z-direction side in place of the pair of leaf springs 14.

When the cover member 33 is located at a first position P1 depicted in FIG. 7 and the distal end of the injection needle 8 is accommodated in the inside space 10 of the cover member 33, the distal end of the leaf spring 14 of the cover member 33 presses the tubular body 6 disposed in the cutout 34 of the catheter main body 32 from the +Z-direction, whereby the tubular body 6 formed of a relatively soft tube is crushed between the leaf spring 14 and the reduced-diameter portion 4, and the lumen 7 of the tubular body 6 is put into a closed state (i.e., is closed).

Figure 8:
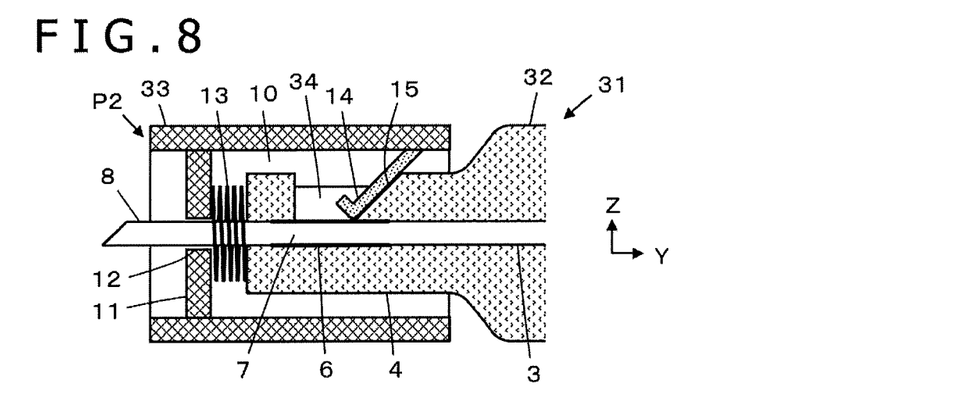
FIG. 8 is a cross-sectional view depicting the medicine injection catheter according to Embodiment 2 when the cover member is located at a second position.

On the other hand, when the cover member 33 is located at a second position P2 depicted in FIG. 8 and the distal end of the injection needle 8 protrudes forward from the inside space 10 of the cover member 33, the leaf spring 14 of the cover member 33 is guided by the inclined surface 15 of the catheter main body 32 and is elastically deformed to such an extent that the distal end of the leaf spring 14 is separated from the outer circumferential portion of the tubular body 6, whereby the lumen 7 of the tubular body 6 is put into an open state (i.e., is open).

In this way, by use of the medicine injection catheter 31 in which the outer circumferential portion of the tubular body 6 is pressed from one side by one leaf spring 14 to be thereby crushed, also, it is possible to achieve simplification of the procedure, to automatically and reliably inject the medicine into the heart tissue synchronously with the beating of the heart, and to prevent the medicine from leaking when the injection needle 8 is drawn out from the inner wall W of the heart, like in the case of the medicine injection catheter 1 according to Embodiment 1.

Embodiment 3

In Embodiment 1 described above, the pair of leaf springs 14 constituting the closing member are attached to the cover member 9, and the pair of inclined surfaces 15 constituting the motion conversion mechanism are formed in the catheter main body 2, but the invention is not limited in this regard. A configuration may also be adopted such that the catheter main body has a closing member and a motion conversion mechanism is attached to the cover member.

Figure 9:
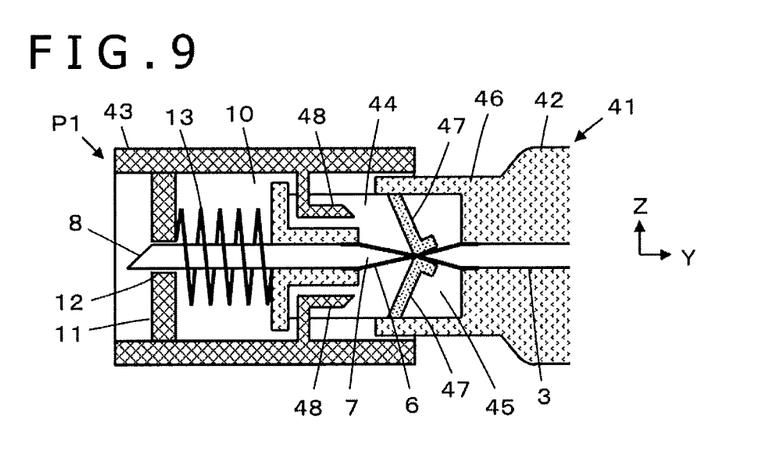
FIG. 9 is a cross-sectional view depicting a medicine injection catheter according to Embodiment 3 when a cover member is located at a first position.

FIG. 9 depicts the configuration of a medicine injection catheter 41 according to Embodiment 3. The medicine injection catheter 41 has a cover member 43 disposed at a distal end portion of an elongated catheter main body 42 in such a manner as to be capable of being advanced and retracted.

Compared to the catheter main body 2 used in the medicine injection catheter 1 of Embodiment 1, the catheter main body 42 is configured in the same manner as the catheter main body 2 of Embodiment 1, except that a reduced-diameter portion 46 formed with an opening portion 44 penetrating in the Z-direction and a recess 45 communicating with the opening portion 44 and recessed toward the proximal end (the +Y-direction side) in regard of the catheter main body 42 along the axial direction, in place of the reduced diameter portion 4 formed with the opening portion 5 and the pair of inclined surfaces 15, and a pair of leaf springs 47 are disposed in the recess 45. A tubular body 6 is disposed such as to be exposed in the opening portion 44 and the recess 45 which communicate with each other.

The pair of leaf springs 47 constitute the closing member, and are disposed at the same Y-directional position. One of the leaf springs 47 is attached to a part located on the most +Z-direction side, of an inner surface of the recess 45 of the reduced-diameter portion 46, and extends substantially in the −Z-direction. The other leaf spring 47 is attached to a part located on the most −Z-direction side, of the inner surface of the recess 45 of the reduced-diameter portion 46, and extends substantially in the +Z-direction. Each of the leaf springs 47 can be elastically deformed in the Y-direction and the Z-direction.

Compared to the cover member 9 used in the medicine injection catheter 1 of Embodiment 1, the cover member 43 is configured in the same manner as the cover member 9 of Embodiment 1, except for having a pair of projecting members (contact pats) 48 which constitute a motion conversion mechanism, in place of the inclined surfaces 15.

One of the projecting members 48 is attached to a part located on the most +Z-direction side, of an inner surface of the cover member 43, extends in the −Z-direction, then is bent and extends in the +Y-direction toward one of the leaf springs 47. The other projecting member 48 is attached to a part located on the most −Z-direction side, of the inner surface of the cover member 43, extends in the +Z-direction, then is bent and extends in the +Y-direction toward the other leaf spring 47. The two projecting members 48 are thus located at diametrically opposite positions in the cover member 43.

When the cover member 43 is located at a first position P1 depicted in FIG. 9 and the distal end of the injection needle 8 is accommodated in the inside space 10 of the cover member 43, the distal ends of the pair of leaf springs 47 pinch and press the tubular body 6 from both sides in the Z-direction, whereby the tubular body 6 formed of a relatively soft tube is crushed between the pair of leaf springs 47, and the lumen 7 of the tubular body 6 is put into a closed state (i.e., the lumen 7 is closed).

Figure 10:
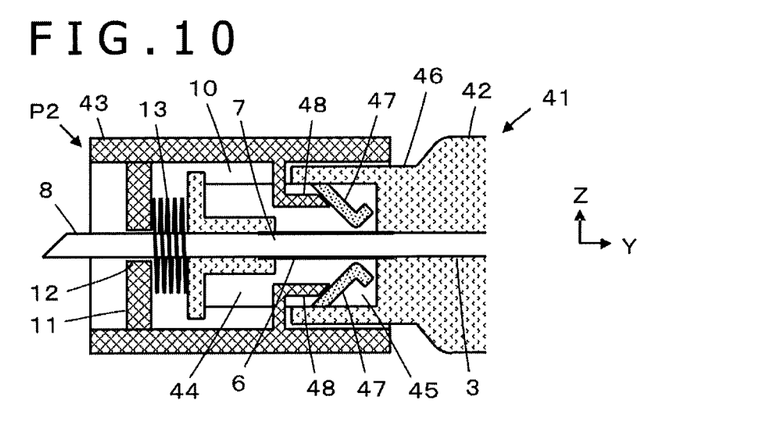
FIG. 10 is a cross-sectional view depicting the medicine injection catheter according to Embodiment 3 when the cover member is located at a second position.

On the other hand, when the cover member 43 is located at a second position P2 depicted in FIG. 10 and the distal end of the injection needle 8 protrudes forward from the inside space 10 of the cover member 43, +Y-directional end portions of the pair of projecting members 48 of the cover member 33 press the corresponding leaf springs 47 in the +Y-direction, whereby the pair of leaf springs 47 are elastically deformed to such an extent that their distal ends are separated from the outer circumferential portion of the tubular body 6, and the lumen 7 of the tubular body 6 is put into an open state (i.e., the lumen is open).

In this way, by use of the medicine injection catheter 41 in which the pair of leaf springs 47 constituting the closing member are attached to the catheter main body 42 and the pair of projecting members 48 constituting the motion conversion mechanism are formed in the cover member 43, also, it is possible to achieve simplification of the procedure, to automatically and reliably inject the medicine into the heart tissue synchronously with the beat of the heart, and to prevent the medicine from leaking when the injection needle 8 is drawn out from the inner wall W of the heart, like in the case of the medicine injection catheter 1 according to Embodiment 1.

In Embodiment 3, also, a configuration may be adopted such that, like in Embodiment 2, the outer circumferential portion of the tubular body 6 is pressed by only one leaf spring 47, not by a pair of leaf springs 47, from one side, to close the tubular body 6.

In addition, the projecting members 48 can be formed from the same material as that for the cover section 33, on condition that the material has such a strength as to deform the leaf springs 47. On the other hand, in the presence of such a reason that the material of the cover section 33 does not have a strength high enough to deform the leaf springs 47, the projecting members 48 can be formed by joining a material different from the material used for the cover section 33.

Embodiment 4

In Embodiment 1 described above, a trap mechanism may further be provided which traps the inner wall W of the heart at a front end portion of the cover member 9 by establishing a negative pressure in the inside space 10 of the cover member 9.

Figure 11:
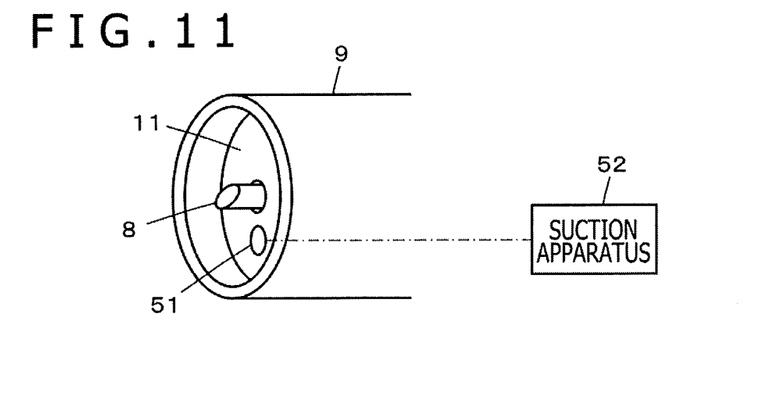
FIG. 11 is a perspective view depicting a distal end portion of a medicine injection catheter according to Embodiment 4.

As depicted in FIG. 11, the trap mechanism of this fourth embodiment includes a suction hole 51 formed in the partition plate 11 of the cover member 9, and a suction apparatus 52 connected to the suction hole 51. The suction apparatus 52 may be, for example, connected to the connector 21 of the medicine injection system depicted in FIG. 4, the catheter main body 2 of the medicine injection catheter 1 may be formed with a suction lumen independently of the medicine supply lumen 3, and the suction apparatus 52 may be connected to the suction hole 51 of the cover member 9 through the suction lumen and the connector 21.

Air in the suction lumen is sucked by the suction apparatus 52 to establish a negative pressure in the inside space 10 of the cover member 9, whereby the inner wall W of the heart is trapped onto the front end portion of the cover member 9, and the medicine can be injected into the heart tissue more reliably.

Such a trap mechanism can similarly be provided also in the medicine injection catheter 31 of Embodiment 2 and in the medicine injection catheter 41 of Embodiment 3.

Embodiment 5

Figure 12:
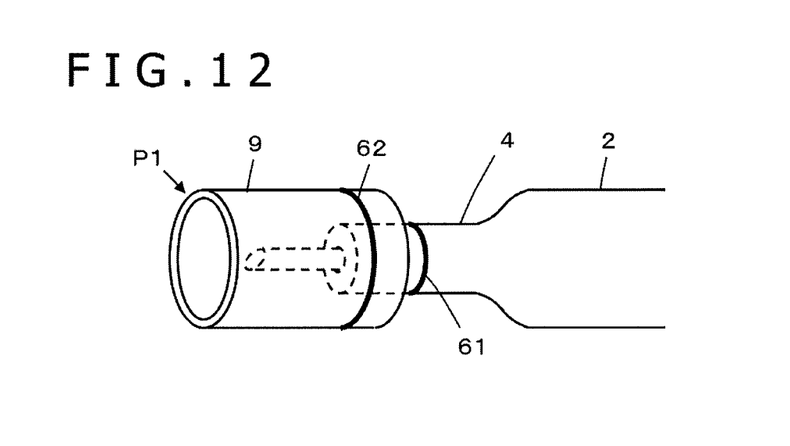
FIG. 12 is a perspective view depicting a medicine injection catheter according to Embodiment 5 when a cover member is located at a first position.
Figure 13:
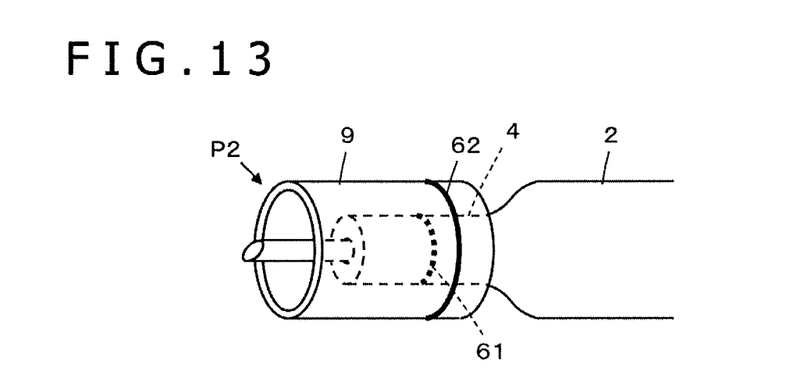
FIG. 13 is a perspective view depicting the medicine injection catheter according to Embodiment 5 when the cover member is located at a second position.

In Embodiment 1 described above, contrast markers 61 and 62 may be disposed respectively at an outer circumferential portion of the reduced-diameter portion 4 of the catheter main body 2 and an outer circumferential portion of the cover member 9, as depicted in FIG. 12. These contrast markers 61 and 62 are for radiographically grasping or locating the positions of the reduced-diameter portion 4 of the catheter main body 2 and the cover member 9 from the outside of a patient when the medicine injection catheter 1 is inserted into the patient's body. The contrast markers 61 and 62 can be formed from a material easy to recognize under radiography, for example, gold, platinum, iridium, tungsten or their alloys, or silver-palladium alloy.

With the position of the reduced-diameter portion 4 of the catheter main body 2 and the position of the cover member 9 grasped or understood by use of such contrast markers 61 and 62, it is possible to judge from an X-ray image whether the cover member 9 is located at the first position P1 or located at the second position P2.

In the cases of the medicine injection catheter 31 of Embodiment 2, the medicine injection catheter 41 of Embodiment 3 and the medicine injection catheter of Embodiment 4, also, the contrast markers can be disposed at both the reduced-diameter portion of the catheter main body and the cover member.

The injection of the medicine has been conducted with the injection needle 8 puncturing the inner wall W of the heart in Embodiments 1 to 5 described above, the injection of the medicine can similarly be performed with the injection needle 8 puncturing an outer wall of the heart. Further, the object to be treated is not limited to the heart, and the medicine injection catheter according to the invention is applicable at the time of injecting a medicine through any of various body walls of a living body, such as inner walls and outer walls of other organs.

As the medicine to be delivered by the various versions of the medicine injection catheter and medicine injection system described above, various therapeutic substances can be used. Examples of the therapeutic effect include reinforcement of the heart wall, a scaffold material, induction of angiogenesis, supplement of cells, and tissue repair or regeneration by prevention of apoptosis or necrosis. Examples of the therapeutic substance include injectable and biocompatible monocomponent or multicomponent materials, polymer-based beads, and polymer hydrogel. Other than these, the examples further include fibrin adhesive, collagen, alginates, synthetic polymer materials such as polyethylene glycol, and chitosan. The therapeutic substance may include only of the above-mentioned material or materials, but this is not limitative. For example, the therapeutic substance may contain cells such as stem cells, e.g., iPS cells, fibroblasts, and skeletal cells, proteins, plasmids, genes, growth factors, chemical attractants, synthetic polypeptides, various pharmaceutical compositions, and, further, other therapeutically useful substances, either singly or in combination.

The detailed description above describes embodiments of a medicine injection catheter and medicine injection system representing examples of the inventive medicine injection catheter and medicine injection system disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:
1. A medicine injection catheter for injecting medicine through a wall of a living body, the medicine injection catheter comprising:
   an elongated catheter main body extending in an axial direction, the catheter main body possessing a distal end and including a medicine supply lumen;
   a tubular body connected to the distal end of the catheter main body, the tubular body including a lumen communicating with the medicine supply lumen;
   an injection needle connected to a distal end of the tubular body, the injection needle possessing a distal end to puncture the wall of the living body and inject the medicine;
   a tubular cover member that includes an inside space in which is accommodated at least the tubular body, the tubular cover member including a distal end adapted to be brought into contact with the living body during use of the medicine injection catheter, the tubular cover member being disposed at a distal end portion of the catheter main body and being configured to undergo advancing and retracting motion along the axial direction of the catheter main body to move between a first position in which the distal end of the injection needle is accommodated in the inside space before the distal end of the cover member is brought into contact with the living body and a second position in which the distal end of the injection needle protrudes distally beyond the distal end of the catheter main body and outside the inside space while the distal end of the cover member is in contact with the living body;
   a closing member that undergoes movement between a lumen closed position in which the closing member closes the lumen of the tubular body to prevent the medicine from flowing to the injection needle and a lumen open position in which the closing member allows the lumen of the tubular body to be open and permit the medicine to flow to the injection needle, the closing member moving between the first and second positions within the inside space of the cover member in a radial direction intersecting the axial direction of the catheter main body;
   a motion conversion mechanism that is configured to automatically convert the retracting motion of the cover member relative to the catheter main body into the movement of the closing member from the lumen closed position to the lumen open position so that the motion conversion mechanism: i) automatically moves the closing member that is in the lumen closed position to the lumen open position in response to the retracting motion of the cover member from the first position to the second position after the distal end of the cover member is brought into contact with the living body; and ii) automatically allows the closing member that is in the lumen open position to move to the lumen closed position in response to the advancing motion of the cover member from the second position to the first position so that when the wall of the living body in contact with the distal end of the cover member moves away from the distal end of the cover member while the medicine is flowing to the injection needle, the closing member moves from the lumen open position to the lumen closed position to close the lumen in the tubular body and stop the medicine from flowing to the injection needle, thereby preventing injection of the medicine at a location other than an intended location; and
   an elastic member which is disposed between the catheter main body and the cover member and which elastically presses the cover member relative to the catheter main body toward the first position.

2. The medicine injection catheter according to claim 1, wherein
the tubular body is flexible,
the closing member includes at least one leaf spring which is attached to an inner surface of the cover member and which presses the tubular body from an outer circumferential surface to close the lumen of the tubular body,
the motion conversion mechanism includes an inclined surface on the catheter main body that is inclined relative to the axial direction of the catheter main body, and
the at least one leaf spring being separated from the inclined surface when the cover member is located at the first position to close the lumen of the tubular body, and the at least one leaf spring being guided by the inclined surface and elastically deformed when the cover member is located at the second position so that the at least one leaf spring is elastically deformed and separated from the outer circumferential surface of the tubular body to thereby open the lumen of the tubular body.

3. The medicine injection catheter according to claim 1, wherein
the tubular body is flexible,
the closing member includes at least one leaf spring which is attached to the catheter main body and which presses the tubular body from an outer circumferential surface to close the lumen of the tubular body,
the motion conversion mechanism includes a projecting member which is attached to an inner surface of the cover member and which extends in the axial direction of the catheter main body toward the at least one leaf spring, and
the at least one leaf spring being separated from the projecting member when the cover member is located at the first position, and the at least one leaf spring being pressed by the projecting member and elastically deformed to close the lumen of the tubular body when the cover member is located at the second position so that the at least one leaf spring is separated from the outer circumferential portion of the tubular body to thereby open the lumen of the tubular body.

4. The medicine injection catheter according to claim 1, wherein the closing member includes a pair of leaf springs which pinch an outer circumferential surface of the tubular body from both sides.

5. The medicine injection catheter according to claim 1, wherein the closing member includes only one leaf spring that presses an outer circumferential surface of the tubular body from one side.

6. The medicine injection catheter according to claim 1, wherein
the cover member includes a partition plate which is fixed in the inside space perpendicular to the axial direction of the catheter main body and which is formed with a through-hole through which passes the injection needle, and
the elastic member is disposed between a front end portion of the catheter main body and the partition plate of the cover member.

7. The medicine injection catheter according to claim 1, further comprising a trap mechanism that establishes a negative pressure in the inside space of the cover member to trap a body wall surface of the living body at a front end portion of the cover member.

8. The medicine injection catheter according to claim 1, wherein the catheter main body and the cover member are each provided with a contrast marker.

9. A medicine injection system comprising:
the medicine injection catheter according to claim 1;
a pressure gauge for detecting a pressure in the medicine supply lumen of the medicine injection catheter;
a medicine supply that supplies medicine into the medicine supply lumen of the medicine injection catheter; and
a control that controls supply of the medicine by the medicine supply section in such a manner that the pressure in the medicine supply lumen of the medicine injection catheter, the pressure being detected by the pressure gauge, is to be constant.

10. A medicine injection catheter for injecting medicine through a wall of a living body, the medicine injection catheter comprising:
a catheter main body extending in an axial direction, the catheter main body possessing a distal end and including a medicine supply lumen configured to receive a medicine supplied from a medicine supply, the medicine supply lumen extending in the catheter main body and opening at the distal end of the catheter main body;
a tubular body connected to the catheter main body and including a lumen in communication with the medicine supply lumen so that medicine in the medicine supply lumen of the catheter main body flows into the lumen in the tubular body, the tubular body possessing a central axis and an outer periphery, the tubular body being comprised of a material that is deformable upon application of a force to the outer periphery of the tubular body to close the lumen in the tubular body and prevent the medicine from flowing through the lumen in the tubular body;
an injection needle connected to the tubular body and possessing a distal end;
the catheter main body, the tubular body and the injection needle being movable together as a unit;
a tubular cover surrounding an interior in which is located at least a portion of the tubular body, the tubular cover including a distal-most end adapted to be brought into contact with the living body during use of the medicine injection catheter, the tubular cover and the catheter main body being relatively movable so that when the distal-most end of the cover is brought into contact with the living body and the injection needle is moved toward the living body during use of the medicine injection catheter the tubular cover and the catheter main body are relatively moved from a first position in which a distal-most end of the injection needle is proximal of the distal-most end of the tubular cover and is covered by the tubular cover to a second position in which the distal-most end of the injection needle protrudes distally beyond the distal-most end of the tubular cover so that the distal-most end of the injection needle is outside the tubular cover to puncture the living body;
a spring that applies a biasing force between the tubular cover and the catheter main body to urge the tubular cover towards the first position relative to the catheter main body;
at least one projection fixed to the catheter main body or the tubular cover and extending inwardly toward the central axis of the tubular body, the at least one projection being movable between a lumen closed position in which the at least one projection contacts the outer periphery of the tubular body when the catheter main body is in the first position relative to the catheter main body so that the at least one projection applies a force to the tubular body that deforms the tubular body and closes the lumen in the tubular body to prevent the medicine from flowing through the lumen in the tubular body, and a lumen open position in which the at least one projection is spaced apart from the outer periphery of the tubular body when the catheter main body is in the second position relative to the catheter main body so that the lumen in the tubular body is open to permit the medicine to flow through the lumen in the tubular body toward the injection needle; and a contact part fixed to and movable together with the tubular cover or the catheter main body;

the contact part being configured to be moved into contact with the at least one projection, from a position spaced from the at least one projection, as the cover and the catheter main body are relatively moved from the first position to the second position so that when the distal-most end of the cover is brought into contact with the living body and the injection needle is moved toward the living body the contact part moves into contact with the at least one projection and automatically moves the at least one projection from the lumen closed position to the lumen open position to thereby permit the medicine to flow to the injection needle;

the contact part being configured to move out of contact with the at least one projection as the cover and the catheter main body are relatively moved from the second position to the first position so that when the wall of the living body in contact with the distal-most end of the cover moves away from the distal-most end of the cover while the medicine is flowing to the injection needle, the at least one projection moves from the lumen open position to the lumen closed position to close the lumen in the tubular body and stop the medicine from flowing to the injection needle, thereby preventing injection of the medicine at a location other than an intended location.

11. The medicine injection catheter according to claim 10, wherein the at least one projection is a leaf spring attached to an inner surface of the cover, and the contact part including an inclined surface at a distal end portion of the catheter main body that is inclined relative to the axial direction of the catheter main body, the leaf spring being in contact with and guided by the inclined surface of the catheter main body when the cover member is in the second position.

12. The medicine injection catheter according to claim 10, wherein the at least one projection is a leaf spring attached to an inner surface of the cover, and the contact part including a projecting member fixed to the cover member and movable together with the cover member, the projecting member contacting the leaf spring when the cover member is located at the second position to move the leaf spring out of contact with the outer periphery of the tubular body so that the lumen in the tubular body is open.

13. The medicine injection catheter according to claim 10, wherein the at least one projection comprises a pair of leaf springs which pinch the outer periphery of the tubular body at diametrically opposite sides of the tubular body.

14. The medicine injection catheter according to claim 10, further comprising a partition plate fixed to the cover so that the partition plate and the cover move together as a unit, the partition plate including a through-hole through which passes the injection needle, and the spring being positioned between the catheter main body and the partition plate.

15. The medicine injection catheter according to claim 10, wherein relative movement of the cover and the catheter main body is guided by two guide projections that are each positioned in a respective guide groove.

16. The medicine injection catheter according to claim 15, wherein the two guide projections are fixed to and extend away from the cover, and the guide grooves are provided in the catheter main body.

17. The medicine injection catheter according to claim 10, wherein the catheter main body and the cover are each provided with a contrast marker.

* * * * *